(12) United States Patent
Majewski et al.

(10) Patent No.: US 7,858,944 B2
(45) Date of Patent: Dec. 28, 2010

(54) DEDICATED MOBILE HIGH RESOLUTION PROSTATE PET IMAGER WITH AN INSERTABLE TRANSRECTAL PROBE

(75) Inventors: Stanislaw Majewski, Yorktown, VA (US); James Proffitt, Newport News, VA (US)

(73) Assignee: Jefferson Science Associates, LLC, Newport News, VA (US)

( * ) Notice: Subject to any disclaimer, the term of this patent is extended or adjusted under 35 U.S.C. 154(b) by 118 days.

(21) Appl. No.: 12/321,666

(22) Filed: Jan. 23, 2009

(65) Prior Publication Data
US 2010/0187424 A1    Jul. 29, 2010

(51) Int. Cl.
*G01T 1/164* (2006.01)
(52) U.S. Cl. .................................. 250/363.03
(58) Field of Classification Search . 250/363.01–363.1; 600/437, 414, 407, 424
See application file for complete search history.

(56) References Cited

U.S. PATENT DOCUMENTS

| | | | |
|---|---|---|---|
| 5,325,855 | A | 7/1994 | Daghighian et al. |
| 6,346,706 | B1* | 2/2002 | Rogers et al. .......... 250/363.04 |
| 6,747,263 | B1 | 6/2004 | Popov |
| 7,115,874 | B2 | 10/2006 | Peter et al. |
| 7,332,722 | B1* | 2/2008 | Tran et al. ............... 250/363.09 |
| 2004/0217292 | A1* | 11/2004 | Moyers et al. ......... 250/363.03 |
| 2005/0082486 | A1* | 4/2005 | Schlyer et al. ......... 250/363.01 |
| 2008/0103391 | A1* | 5/2008 | Dos Santos Varela ....... 600/436 |
| 2009/0030310 | A1* | 1/2009 | Hamill et al. ............... 600/437 |
| 2010/0056900 | A1* | 3/2010 | Whitcomb et al. .......... 600/414 |

OTHER PUBLICATIONS

Huh et al., "Investigation of an internal PET probe for prostate imaging," 2007, Nuclear Instruments and Methods in Physics Research A, vol. 579, pp. 339-343.*
Huh et al., "An invetigation of an intra-operative PET imaging probe," 2007, IEEE Nuclear Science Symposium Conference Record, vol. 1, pp. 552-555.*
Raylman et al., "Development of a dedicated positron emission tomography system for the detection and biopsy of breast cancer," 2006, Nuclear Instruments and Methods in Physics Research A, vol. 569, pp. 291-295.*
Guerra et al., "State-of-the-art PET, SPECT and CT for small animal imaging," 2007, Nuclear Instruments and Methods in Physics Research A, vol. 583, pp. 119-124.*
Qi, "Optimization of a PET scanner design for prostate lesion detection," 2004, IEEE Proceedings of the 26th Annual International Conference of the IEEE EMBS, pp. 1357-1360.*

(Continued)

*Primary Examiner*—David P Porta
*Assistant Examiner*—Kiho Kim

(57) ABSTRACT

A dedicated mobile PET imaging system to image the prostate and surrounding organs. The imaging system includes an outside high resolution PET imager placed close to the patient's torso and an insertable and compact transrectal probe that is placed in close proximity to the prostate and operates in conjunction with the outside imager. The two detector systems are spatially co-registered to each other. The outside imager is mounted on an open rotating gantry to provide torso-wide 3D images of the prostate and surrounding tissue and organs. The insertable probe provides closer imaging, high sensitivity, and very high resolution predominately 2D view of the prostate and immediate surroundings. The probe is operated in conjunction with the outside imager and a fast data acquisition system to provide very high resolution reconstruction of the prostate and surrounding tissue and organs.

17 Claims, 7 Drawing Sheets

OTHER PUBLICATIONS

Cinti et al., "CsI(Tl) micro-pixel scintillation array for ultra-high resolution gamma-ray imaging," 2007, IEEE Transactions on Nuclear Science, vol. 54, No. 3, pp. 460-474.*

Llosa et al., "Silicon photomultipliers and SiPM matrices as photodetectors in nuclear medicine," 2007, IEEE Transactions on Nuclear Science Symposium Conference Record, vol. 5, pp. 3220-3223.*

Osovizky et al, "Scintillation light readout using silicon photomultiplier-Review and Experimental Results," 2008, IEEE Nuclear Science Symposium Conference Record, vol. 1, pp. 2482-2483.*

N. Clinthorne, "Promise of the Compton prostate probe, recent results and beyond", presented at the Topical Symposium on Advanced Molecular Imaging Techniques in the Detection, Diagnosis, Therapy, and Follow-Up of Prostate Cancer, Dec. 6-7, 2005, Rome, Italy.

J. S. Huber et al., "Dual-Modality PET/Ultrasound imaging of the Prostate", Lawrence Berkeley National Laboratory. Paper LBNL-59114. (Nov. 11, 2005).

J. S. Huber et al., "Initial Results of a Positron Tomograph for Prostate Imaging", IEEE Transactions on Nuclear Science, vol. 53, Issue 5, Part 1, Oct. 2006 pp. 2653-2659.

S. S. Huh et al., "Investigation of an internal PET probe for prostate imaging", accepted for publication in Nuclear Instruments and Methods in Physics Research, 2007.

C. Levin, "New Photon Sensor Technologies for PET in Prostate-Specific Imaging Configurations", presented at the Topical Symposium on QAdvanced Molecular Imaging Techniques in the Detection, Diagnosis, Therapy, and Follow-Up of Prostate Cancer, Dec. 6-7, 2005, Rome, Italy.

W. Moses, "Dedicated PET Instrumentation for prostate imaging", presented at the Topical Symposium on Advanced Molecular Imaging Techniques in the Detection, Diagnosis, Therapy, and Follow-Up of Prostate Cancer, Dec. 6-7, 2005, Rome, Italy.

V. Popov et al., "A Novel Readout Concept for Multianode Photomultiplier Tubes with Pad Matrix Anode Layout", Nuclear Instruments and Methods in Physics Research A 567 (2006) 319-322).

V. Popov et al., "Study of Photonis XP1470 Nine-Channel Photomultiplier Tube For Applications in High Resolution Single Gamma and PET Imagers", presented at the 2007 IEEE MIC conference, Honolulu, Hawaii, Oct. 27-Nov. 3, 2007.

J. Proffitt et al.; "A flexible high-rate USB2 data acquisition system for PET and SPECT imaging", 2005 IEEE Nuclear Science Symposium Conference Record, Puerto Rico, Oct. 23-29, 2005, pp. 2971-2975.

J. Proffitt et al., "Implementation of a High-Rate USB Data Acquisition System for PET and SPECT Imaging", 2006 IEEE Nuclear Science Symposium Conference Record, San Diego, California, Oct. 29-Nov. 1, 2006, pp. 3063-3067.

T. G. Turkington et al., "PET prostate imaging with small planar detectors", T.R.QNuclear Science Symposium Conference Record, 2004 IEEEQvol. 5, Issue , Oct. 16-22, 2004 pp. 2806-2809.

* cited by examiner

DEDICATED MOBILE HIGH RESOLUTION PROSTATE PET IMAGER WITH AN INSERTABLE TRANSRECTAL PROBE

The United States of America may have certain rights to this invention under Management and Operating contract No. DE-AC05-06OR23177 from the Department of Energy.

FIELD OF THE INVENTION

This invention relates to diagnostic imaging and more particularly to a high resolution PET imaging system for imaging the prostate gland and surrounding organs in a patient.

BACKGROUND OF THE INVENTION

In the current state of the art, standard PET imagers are bulky devices that are placed in dedicated imaging rooms and require the patient to be transported to the imager. These standard imagers have poor spatial resolution that is inadequate for accurate imaging of small organs such as the prostate. In addition, in some clinical situations, there would be an advantage to having a dedicated imager that can be, for example, assisting in the surgery suite where imaging can provide immediate biopsy guidance of (suspected) cancerous lesions, and with cancerous tissue removal both from prostate and from surrounding tissue.

Existing mobile PET imagers do not satisfy the special combined requirements of size, resolution and sensitivity for prostate imaging tests.

A dual-modality prostate PET imager with transrectal ultrasound (TRUS) was described in "Initial Results of a Positron Tomograph for Prostate Imaging", J. S. Huber et al., IEEE Transactions on Nuclear Science, Volume 53, Issue 5, Part 1, October 2006 Page(s): 2653-2659. TRUS provides anatomical details that can be co-registered with a PET image. This PET imager was constructed from sectors of a standard ECAT HR+ PET with spatial resolution limited to approximately 4-5 mm FWHM. The geometry was closer than standard ring geometry which introduces additional depth of interaction error.

The concept of high-resolution PET imaging in the pelvis region with dual planar detectors has been investigated. For example, see "PET prostate imaging with small planar detectors", T. G. Turkington et al., T.R.Q Nuclear Science Symposium Conference Record, 2004 IEEEQ Volume 5, Issue, 16-22 Oct. 2004 Page(s): 2806-2809. The scanner consisted of two 20 cm×15 cm (axial) planar detectors made of 3 mm×3 mm×10 mm LGSO scintillator detection elements. The detector heads were mounted on a rotating gantry with adjustable detector radii. Although detection of hot lesions in the pelvis with small dual planar PET detectors was judged to be possible, better characterization of such lesions requires detector orbiting or larger detectors.

A transrectal high resolution (~1 mm) prostate imager 20 including a PET probe 21 operating in conjunction with a small field of view outside imaging detector 22 and placed by the pelvis region close to the prostate 23, see FIGS. 1 and 2, was proposed by C. Levin in "New Photon Sensor Technologies for PET in Prostate-Specific Imaging Configurations", and by W. Moses in "Dedicated PET Instrumentation for prostate imaging", both of which were presented at the Topical Symposium on Advanced Molecular Imaging Techniques in the Detection, Diagnosis, Therapy, and Follow-Up of Prostate Cancer, 6-7 Dec. 2005, Rome, Italy. The prior art probe 21 is behind the prostate 23 and the outside detector 22 is in front of the prostate 23 and serves as a second coincident detector to the probe. The outside detector 22 captures the second coincident 511 keV gamma ray originating from the positron emissions and annihilations in the prostate and in surrounding tissue. The outside detector is placed in a fixed position and includes a limited field of view. In this approach, the limited detector size and limited angular sampling of the imaging procedure does not allow for full scale all-angle 3D tomographic imaging of the prostate region and of surrounding organs.

Other hybrid imaging systems using conventional PET have been proposed, see Sam S. Huh et al., "Investigation of an internal PET probe for prostate imaging", accepted for publication in Nuclear Instruments and Methods in Physics Research, 2007. A hybrid imaging system 25 with conventional PET, as shown in FIG. 3, includes an external PET ring 26 and combines a conventional PET imager 22 with an add-on transrectal probe 27 to image the prostate 28. A simulation study was performed of a high-resolution imaging probe in coincidence with a conventional external PET scanner. The internal detector provides both high resolution (~1 mm FWHM) and high efficiency while events recorded by the standard PET provide complete tomographic data for image reconstruction. The concept is still under simulation investigation to estimate the performance in comparison with conventional PET.

A PET system with an insertable probe 29, shown in exploded and assembled form in FIG. 4, as one of the detectors has been proposed by C. Levin, "New Photon Sensor Technologies for PET in Prostate-Specific Imaging Configurations", presented at the Topical Symposium on QAdvanced Molecular Imaging Techniques in the Detection, Diagnosis, Therapy, and Follow-Up of Prostate Cancer, 6-7 Dec. 2005, Rome, Italy. The second detector would be placed outside the patient on the other side of the prostate in order to capture the second coincident 511 keV gamma ray. Unfortunately, this approach has limited angular sampling of the imaged organ.

There are practical implementation issues related to the use of insertable transrectal probes. They cannot be treated as non-invasive, with the related patient safety issues involving active probes. There are limits to the useful detection volume, probe positioning relative to prostate, and non-uniformity of sensitivity for different parts of prostate. Insertable probes, while being close to parts of the prostate, will not image enough surrounding tissue.

As described above, although some imaging geometries have been proposed for the prostate, there is still a need for a reliable PET imager capable of providing torso-wide imaging of the prostate and surrounding tissues with a wide active field of view and with a sufficiently high resolution for full scale all-angle 3D tomographic images.

SUMMARY OF THE INVENTION

The invention provides a dedicated mobile PET imaging system to image the prostate and surrounding organs. The imaging system includes an outside high resolution PET imager placed close to the patient's torso and an insertable and compact transrectal probe that is placed in close proximity to the prostate and operates in conjunction with the outside imager. The two detector systems are spatially co-registered to each other. The outside imager is mounted on an open rotating gantry to provide torso-wide 3D images of the prostate and surrounding tissue and organs. The insertable probe provides closer imaging, high sensitivity, and very high resolution predominately 2D view of the prostate and immediate surroundings. The probe is operated in conjunction with the outside imager and a fast data acquisition system to provide very high resolution reconstruction of the prostate and surrounding tissue and organs.

OBJECTS AND ADVANTAGES

Several advantages are achieved with the dedicated prostate PET imager system with insertable probe of the present invention, including:
(1) The imager will provide a large active field of view including torso-wide (40 cm or more) by at least 10 cm wide.
(2) The outside imager includes detector modules placed in front of the patient and behind the patient to improve reconstruction resolution of the prostate region.
(3) The outside imager will provide a 3D reconstruction resolution of 1.5-2.0 mm (over body slice involved).
(4) A reconstruction resolution of 1.0-1.5 mm 2D will be provided with the probe in coincidence with the outside imager (over the small field of view of the probe).
(5) A rotating open geometry gantry will enable 360 deg angular sampling in the 3D imaging mode with the outside imager.
(6) The transrectal probe of the current invention will image a larger portion of the tissue surrounding the prostate as compared to prior art probes.
(7) The prostate imager includes a multi-channel fast data acquisition and processing system capable of recording data with at least 200 kHz trigger rate in a list mode to enable prompt limited data analysis and fast data replay and image reconstruction during the same scan session.

These and other objects and advantages of the present invention will be better understood by reading the following description along with reference to the drawings.

Figure 1:
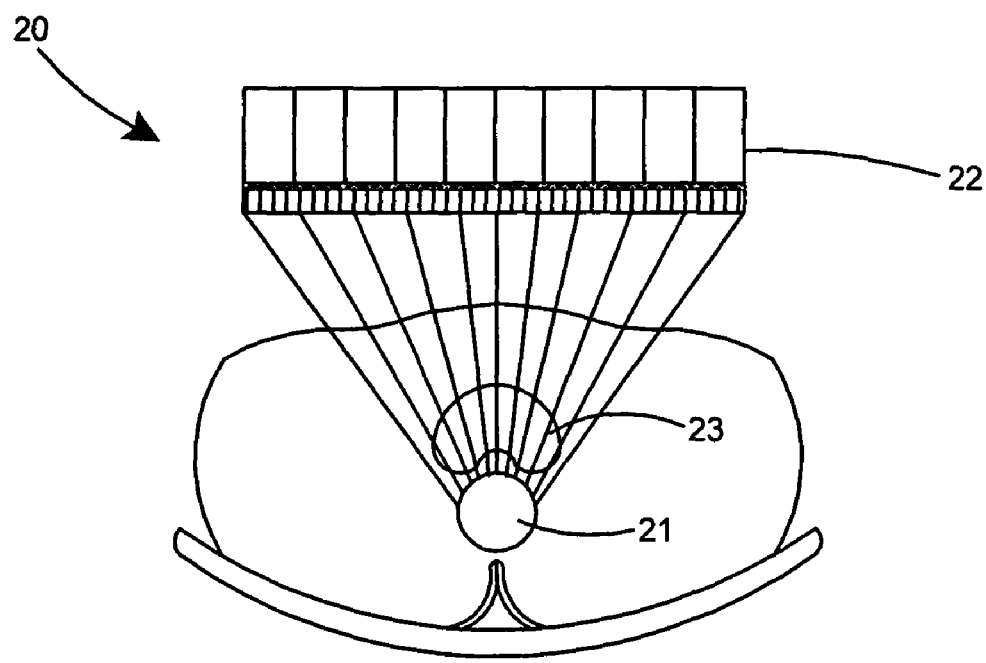
FIG. 1 is a transaxial view of a prior art prostate imager including an outside limited field of view imaging detector and a transrectal probe placed behind and close to the prostate gland.
Figure 2:
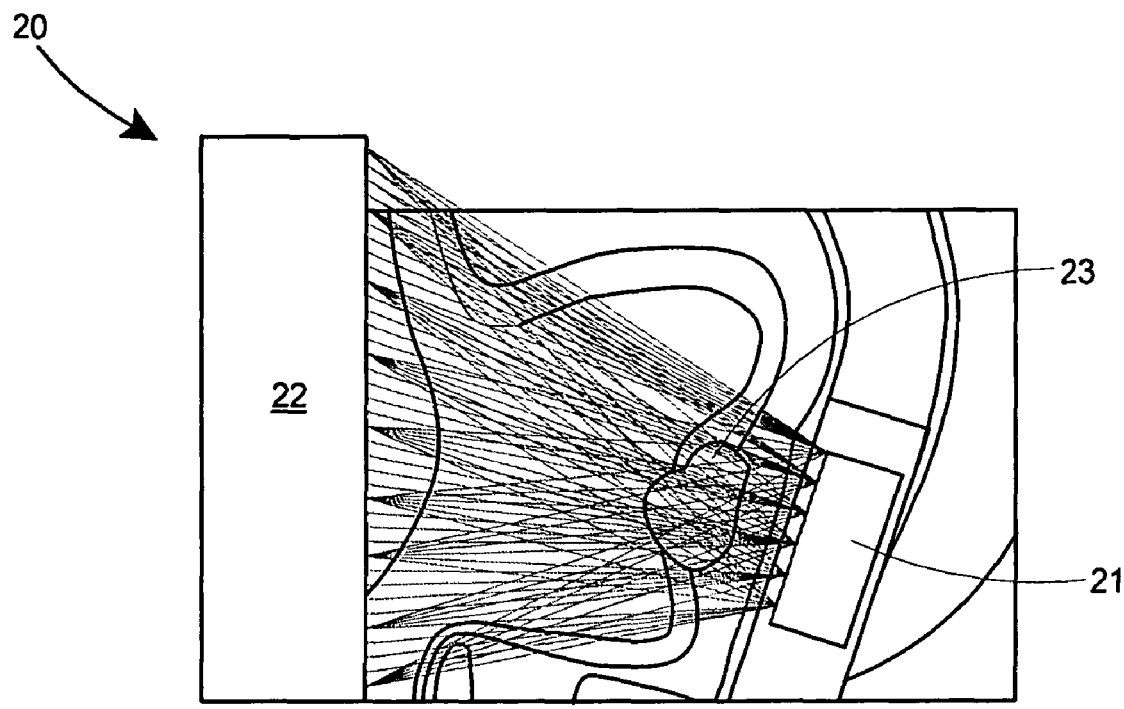
FIG. 2 is a closer side view of the prior art imager of FIG. 1 shown with some coincidence lines of response.
Figure 3:
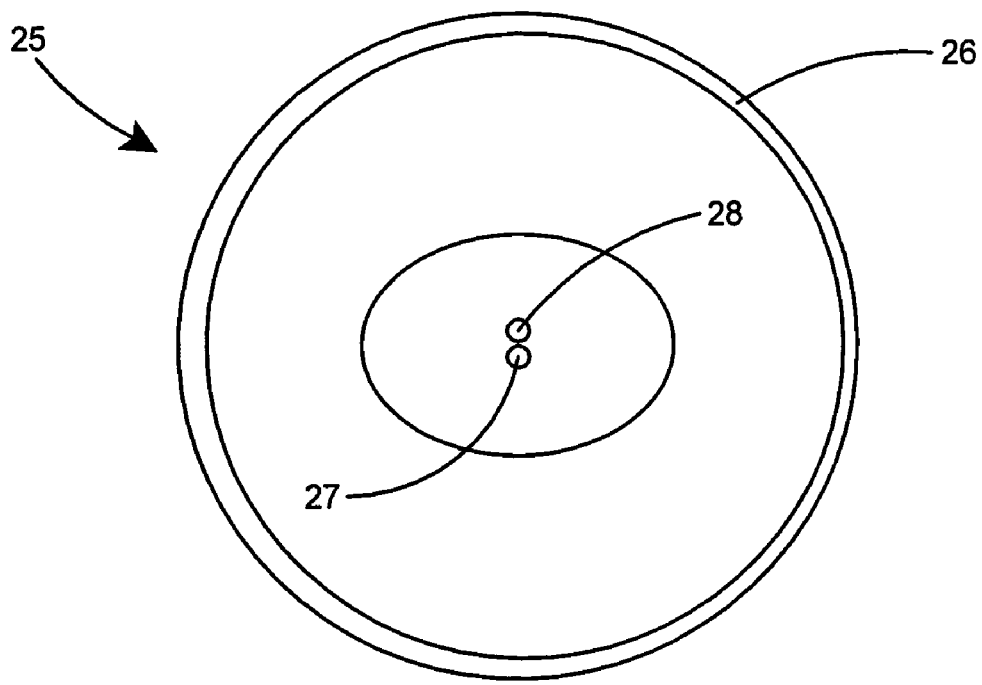
FIG. 3 is a schematic of a prior art hybrid imaging system combining standard PET with an add-on transrectal probe.
Figure 4:
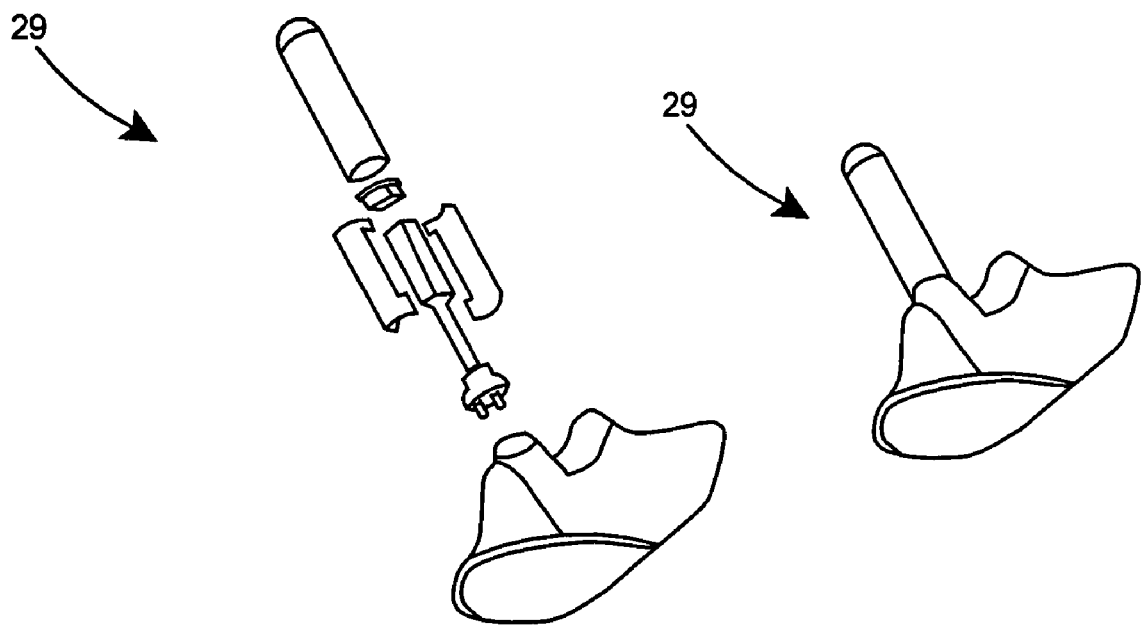
FIG. 4 depicts exploded and assembled perspective views of a prior art transrectal probe.

INDEX TO REFERENCE NUMERALS IN DRAWINGS 20 prior art prostate imager
21 PET probe
22 outside imaging detector
23 prostate
25 hybrid imaging system with conventional PET
26 external PET ring
27 prior art transrectal probe
28 prostate
29 prior art insertable probe
30 outside PET imager
32 detector section
34 patient
36 patient bed
37 detector super-module
38 direction of angular rotation
39 prostate region
40 dedicated prostate imager
41 external or outside PET imaging system
42 internal transrectal PET probe
43 front external detector module
44 rear external detector module
45 detector section or head
46 patient
47 mobile patient bed
48 line of response
50 prostate
51 rotatable mobile gantry
52 direction of angular rotation
53 direction of distance adjustment between detection modules
54 outside imager section or head
55 array of flat PSPMTs
56 PSPMT
57 scintillator sensor
58 pixellated or scintillation array
59 optical window
60 outer window
61 dead region
62 reflective strip
63 outer shell or shield
70 compact silicon imaging module or detector
72 basic silicon imaging module
74 basic SiPM unit or pad
75 dead space
76 readout channel with 4 pads
78 readout channel with 16 pads
80 SiPM sensor unit
82 scintillator array
84 light guide
86 SiPM array
88 preamplifier W width of detector head
Wp width of probe detector head
Lp length of probe detector head

DETAILED DESCRIPTION OF THE INVENTION

According to the present invention, a dedicated mobile high resolution PET imager to image the prostate and surrounding organs combines two major components including an outside high resolution dedicated PET imager placed close to the patient's torso with an insertable compact transrectal probe that is placed close to the prostate. The insertable probe operates in conjunction with the outside imager. The two detector systems are spatially co-registered to each other via electronic sensor positioning systems placed on all detector modules. The outside imager mounted on an open rotating gantry provides torso-wide 3D images of the prostate and surrounding tissue and organs. The insertable probe provides closer high sensitivity and very high resolution but limited, mostly 2D, view of the prostate and immediate surroundings. While the outside imager can operate separately, the critical focus of the present invention is the operation of the probe in conjunction with the outside imager in a mobile, open geometry organ-specific structure. Open structure of the system can allow for implementation of the system in therapy and surgical situations.

Figure 5:
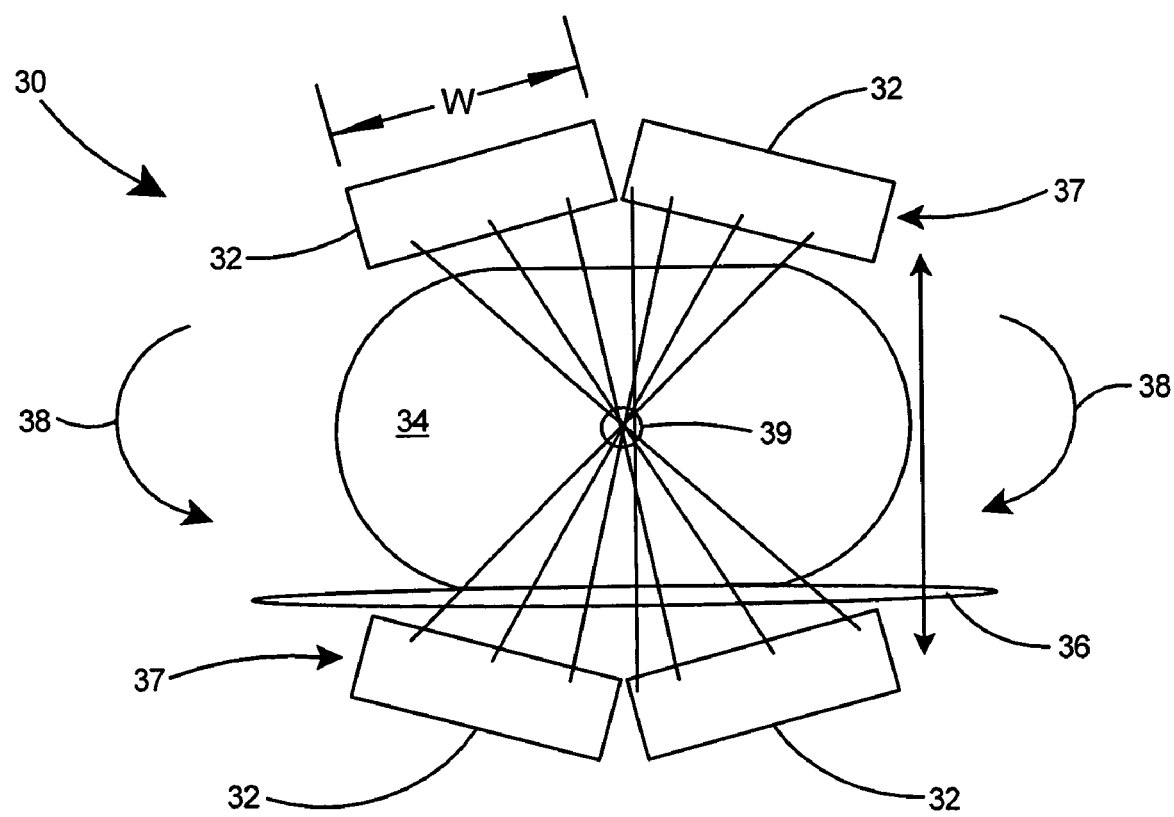
FIG. 5 is a transaxial view of the outside imager of the prostate PET imager of the present invention with four mechanically separate detector sections placed above and below a patient placed on a bed.

With reference to FIG. 5, there is shown a transaxial view of the outside imager portion 30 of the prostate PET imager of the present invention. The outside or external component 30 of the prostate PET imaging system includes four mechanically separate detector sections 32 placed above and below a patient 34 placed on patient bed 36, as close as possible to the patient's body. The detector sections 32 have a width W of 20-30 cm. Two detector sections 32 form a detector super-module 37 with the flexible relative angular arrangement, 15-25 degrees as shown by directional arrows 38, to better view the prostate region 39 and to optimize tomographic 3D spatial resolution. This is also an economically optimal configuration with minimally sized imager for high performance imaging. The detector sections 32 can be used either in a static mode or mounted to the rotating gantry and then rotated in a limited angular range to provide full angular projective sampling of the prostate region for best tomographic 3D reconstruction.

Figure 6:
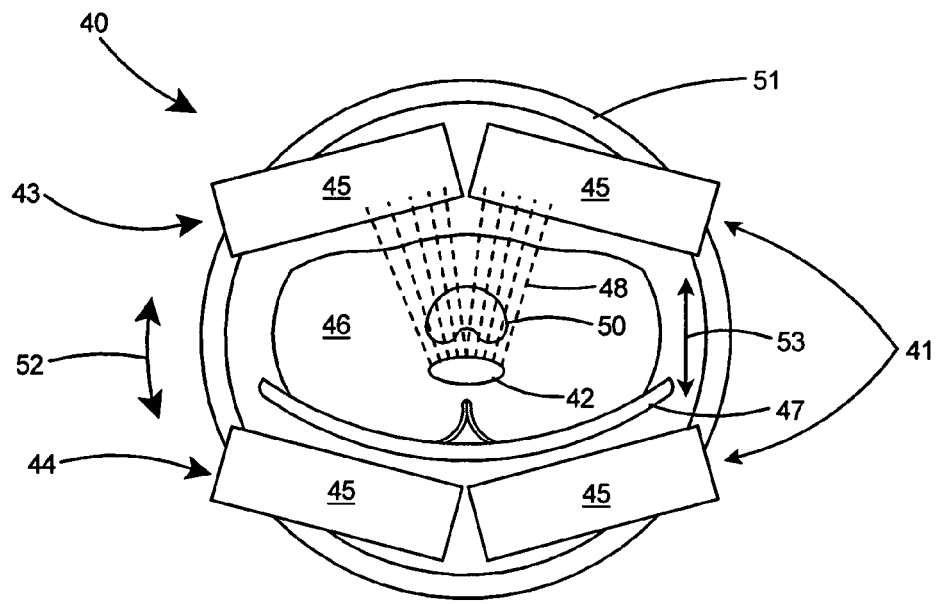
FIG. 6 is transaxial view of the dedicated prostate imager combining the external imaging system and the internal probe.

Referring to FIG. 6 there is shown a schematic of the preferred embodiment of the dedicated prostate imager 40 combining the dedicated external or outside PET imaging system 41 and the internal transrectal PET probe 42. The external imaging system 41 includes front external detector modules 43 and rear external detector modules 44. The outside imaging system 41 includes four mechanically separate detector sections or heads 45 placed above and below a patient 46 placed on a mobile patient bed 47, as close as possible to the patient's body. Examples of lines of response 48 along the paths of back to back coincident 511 keV annihilation gamma rays, between the front external modules 43 and the internal probe 42 are shown as phantom lines. The left-most line of response is coming from the tissue outside the prostate 50. The detector sections 45 are mounted to a rotating open geometry mobile gantry 51 and to enable rotation of the detector sections 45 in an angular range of approximately 15 to 25 degrees, as shown by directional arrows 52, to provide full angular projective sampling of the prostate region for best tomographic 3D reconstruction. As shown by directional arrow 53, the distance between the front external detector modules 43 and rear external detector modules 44 can be adjusted, preferably with an adjustment distance of at most 25 cm.

A dedicated mobile high resolution PET imager 40 according to the present invention will include a multi-channel fast Data Acquisition (DAQ) system and fast data acquisition software to process and save data digitized in the DAQ system. Low voltage and high voltage power supplies will be included for onboard readout electronics on the detector heads 45. An electronic positioning system is included to control absolute and relative positioning of all the outside detector modules 43 and 44, the probe 42 and the rotatable open geometry mobile gantry 51. The dedicated prostate imager 40 will include a mobile cabinet with computer, trigger and data acquisition electronics, and power supplies and an optional mobile patient bed 47. Additionally, tomographic reconstruction software can be provided with the imaging system 40.

The dedicated mobile high resolution PET imager 40 of the present invention will provide an active field of view that is torso-wide (at least 40 cm) by at least 10 cm wide. The outside imager will achieve a 3D reconstruction resolution of at least 1.5-2.0 mm (over body slice involved). The probe 42 in coincidence with the outside imager 41 will provide at least 1.0-1.5 mm 2D reconstruction resolution over the small field of view of the probe. The rotating open geometry gantry 51 enables 360 degree angular sampling in the 3D imaging mode with the outside imager 41. The multi-channel fast data acquisition and processing system is capable of recording data with at least 200 kHz trigger rate in a list mode, to enable prompt limited data analysis, and fast data replay and image reconstruction during the same scan session.

The operation of the dedicated mobile high resolution PET imager 40 of the present invention will be explained with reference to FIG. 6. The imaging procedure will combine the advantages of the two imaging detector components including the external PET detector 41 and the internal PET probe 42. The outside imaging system 41 will produce, with high resolution and moderate sensitivity, images of the whole region of interest, including prostate 50 and surrounding organs and tissue. The transrectal probe 42 will provide the "magnified" very high resolution and high sensitivity image of the limited region of the prostate. A potential initial imaging procedure will first obtain the view of the torso slice with the outside detector 41, and for closer inspection of the prostate region the probe 42 will be inserted. Alternatively, the probe 42 can be used first to look for uptake hot spots or lesions and then this will be followed with a broader view tomographic scan obtained with the outside PET system 41. The size of the probe 42 can allow for small scanning of the region of the prostate 50, to cover all the interesting spots in the imaging inspection procedure. The positioning system installed on the probe 42 and outside detectors 45 will allow for co-registration of the two types of images.

Outside and inside imaging can be also used in a repeated sequence with more than two separate imaging fragments of the full procedure. Finally, in principle imaging with both parts 41 and 42 of the system can be done at the same time, with the probe 42 and the front outside modules 43 providing local enhanced view, while the front 43 and back outside imaging modules 44 providing the broader view.

Several imaging technologies can be implemented in the dedicated mobile high resolution PET imager 40 of the present invention. The preferred PET imager will have a scintillator as a sensor/energy converter of the 511 keV annihilation gamma rays, while different photodetectors can serve as detectors of the scintillation light produced by the absorbed 511 keV gamma rays in the scintillator gamma sensor. The scintillator sensor part can be made of pixellated or plate crystal scintillator materials such as LSO, LYSO, GSO, BGO, LaBr3, NaI(Tl), CsI(Tl), or CsI(Na).

The photodetector part in general can be a standard or multi-element photomultiplier, position sensitive, flat panel or microchannel plate based photomultiplier, avalanche photodiode arrays or large size avalanche photodiodes with resistive etc readout, and different variants of the novel so-called silicon photomultiplier. The photodetector can include light guides such as simple plates, fiberoptic straight or tapered light guides, bunches of straight or bent fibers.

However, the requirements of a compact insertable probe limit the above choices to a much smaller group of options. In principle, photomultipliers can be still employed when placed outside the patient's body with properly designed fiberoptic light guide schemes, but practically such an optical coupling scheme will be very difficult to implement due to size limitations. Therefore, the design of the transrectal probe will be limited to solid state photodetectors such as avalanche photodiodes or silicon photomultipliers with the same choices of scintillators as used in outside detectors.

Figure 7:
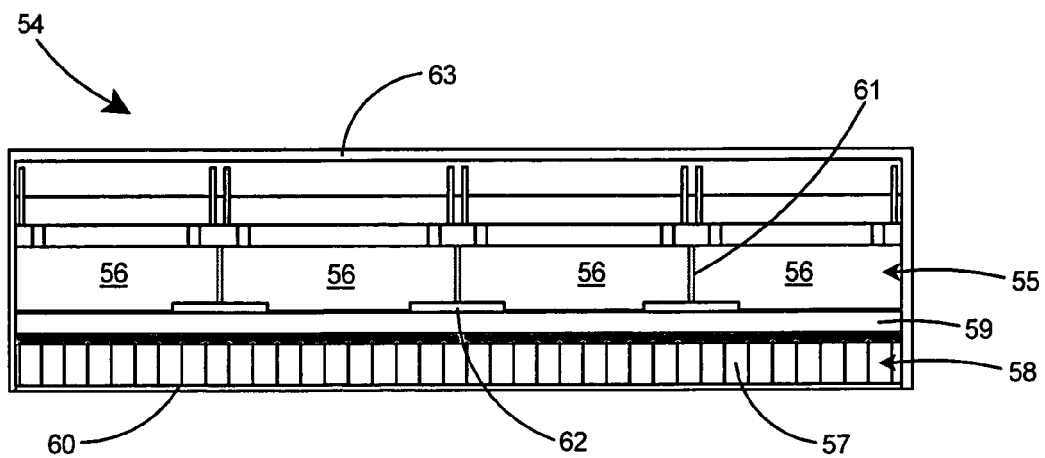
FIG. 7 is a sectional view of a proposed design of an outside detector module according to the present invention.

The outside imager section or head 54 of a preferred scintillator/photodetector type can include a contiguous array 55 of flat position sensitive photomultiplier tubes (PSPMTs) 56 coupled to a scintillator sensor 57 in the form of pixellated array 58 as shown in FIG. 7. The scintillator array 58 can be additionally encapsulated in an air tight container with a thin optical window 59 on the side of the PSPMT array 55. The outer window 60 of the scintillation array 58 is a thin (~1 mm of aluminum or equivalent) protection sheet or shell for light tightness and mechanical protection. An additional coupler window is implemented to permit better optical coupling of the light emerging from the scintillator pixels that are in front of the dead regions 61 between individual flat panel PSPMT units 56. To further improve light collection from these regions, narrow reflective/diffusive strips 62 are placed in the dead regions 61 to reflect light going into the dead regions and by this to increase the fraction of this scintillation light being collected at the photocathodes of the PSPMTs 56 after additional reflection, scattering and diffusion. In the imager head 54 depicted in FIG. 7, PSPMTs of approximate 5 cm×5 cm size such as Hamamatsu H8500 or H9500 PSPMTs are used, to obtain coverage of about 20 cm per detector module 54. The H8500 and H9500 PSPMTs are available from Hamamatsu Corporation of Bridgewater, N.J.

Typically a plastic or metal outer shell or box 63 with opening in front of the scintillation array 58 encloses the detector 54. A special variant of the box 63 is to implement a high Z material such as tungsten or lead or an alloy or mixture of these metals with other metals in the side walls and the back plate to shield the detector head 54 from the scattered gamma radiation background arriving from all other sides than the front of the detector. The housing provides a structural container for the detector head 54 and a means for attaching it to the fixtures and the gantry and enabling detector head placement in the vicinity of the patient's torso.

The preferred embodiment of the outside imager is composed of individual detection modules 54, each based on a Hamamatsu H8500 flat panel PMT coupled to an array of 24×24 LYSO 2×2×15 mm pixels with a 2.1 mm pitch. Each module has four analog position outputs and one (fast) energy output. The position outputs are recorded and digitized in the DAQ system to calculate position of the interacting 511 keV gamma ray. The fast sum signal is used to create the coincident trigger events in the trigger electronics, and then provided to the DAQ system to record the event data from the detector modules. The optimal on-board readout design will include PMT gain uniformity correction assuring high energy and spatial resolutions and high rate performance with minimal number of readout channels.

An alternative more economical embodiment for the basic detection module of the outside detector heads can be based on multi-element PMTs such as small-profile 2" square nine-element Photonis XP1470 PMTs. However, while the achieved intrinsic spatial resolution was only marginally satisfactory for 2 mm pitch scintillation pixels, these PMTs are much slower than H8500 PSPMTs, primarily due to time shifts between the individual nine inner channels. Partial remedy schemes are in principle possible but the readout design and calibrations become more complicated and complete problem correction is not possible. The system built on these PMTs would be also much more bulky.

Figure 8:
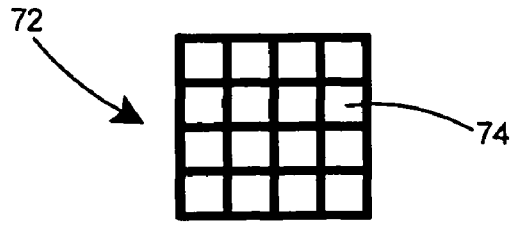
FIG. 8 is an elevation view of a basic SiPM imaging module including an array of 4×4 3 mm square active pads.
Figure 9:
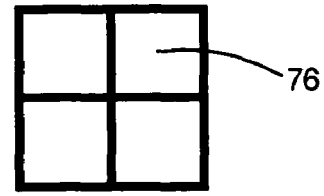
FIG. 9 is an elevation view of the 3 mm pads from the basic module of FIG. 9 with four pads connected to one readout channel.
Figure 10:
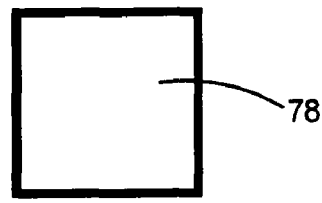
FIG. 10 is an elevation view of the 3 mm pads from the basic module of FIG. 9 with all sixteen pads connected to one readout channel.
Figure 11:
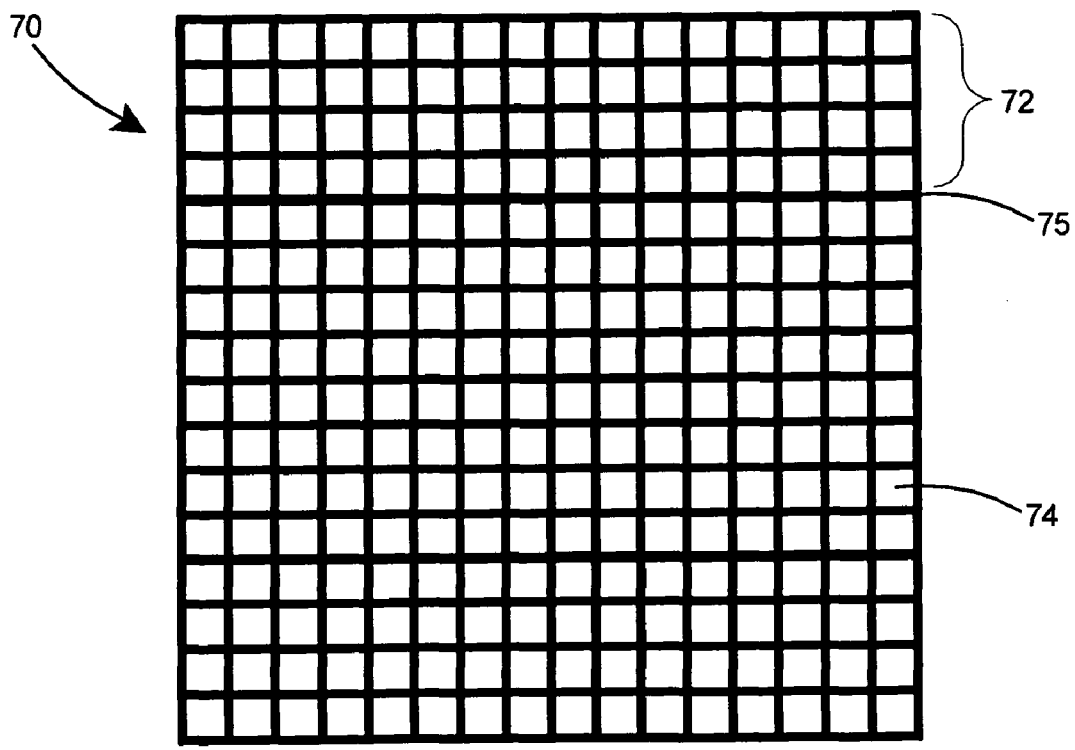
FIG. 11 is an elevation view of a plug-in PMT replacement module according to the present invention that includes arrays of 16 (4×4) basic SiPM imaging modules.

In another preferred example of the outside detector head, Silicon Photomultipliers SiPMs can be used in lieu of the position sensitive PMTs. Typically SiPM modules come in smaller units of about 3 mm in size. Therefore, for the outside detector, arrays of these devices are needed to cover the desired active field of view. Referring to FIGS. 8-11 there is shown an example of how to achieve a SiPM photodetector 70 of approximately 5 cm×5 cm active field of view using nominal 12.5 mm modules 72 composed of sixteen 3 mm basic SiPM units 74. As shown in FIG. 8, the basic initial imaging module 72 can have an array of sixteen 3 mm×3 mm readout pixels/pads 74 arranged in a 4×4 array. These basic imaging modules 72 will be four-side buttable with an estimated 1 mm dead space 75 at the edges. The 3 mm pads 74 from the basic module 72 can be either read separately or coarsely with four pads connected to one readout channel 76 (see FIG. 9) or all 16 pads connected to one readout channel 78 (see FIG. 10). The plug-in PMT replacement module of about 5 cm$^2$ in size shown in FIG. 11 will be implemented by arranging arrays of 16 (4×4) basic imaging modules 72 to form compact imaging modules 70 equivalent for example to H8500/H9500 flat panel PMTs from Hamamatsu. These modules 72 can be arranged in compact imaging modules 70 composed of 4×4 basic modules 72, with coverage and readout needs equivalent to the H8500/9500 PSPMT. In this multi-step modular approach, and with properly designed on-board readout circuitry, the switch between the two photodetector technologies (flat PSPMT to SiPM) can be of a plug-in replacement type with minimized complications and costs during the switch. Use of this compact photodetector 70 will minimize the size of the outside imaging system.

Silicon PM is the preferred photodetector technology for the necessarily compact transrectal probe 42. The limited imaging geometry between the probe 42 and the front external detector module 43 allows practically only for very high resolution planar PET imaging. Therefore, the preferred design of the transrectal probe, still allowing for high spatial 2D resolution (projective geometry), is a flat-type module with one scintillator layer coupled to a compact photodetector array.

Figure 12:
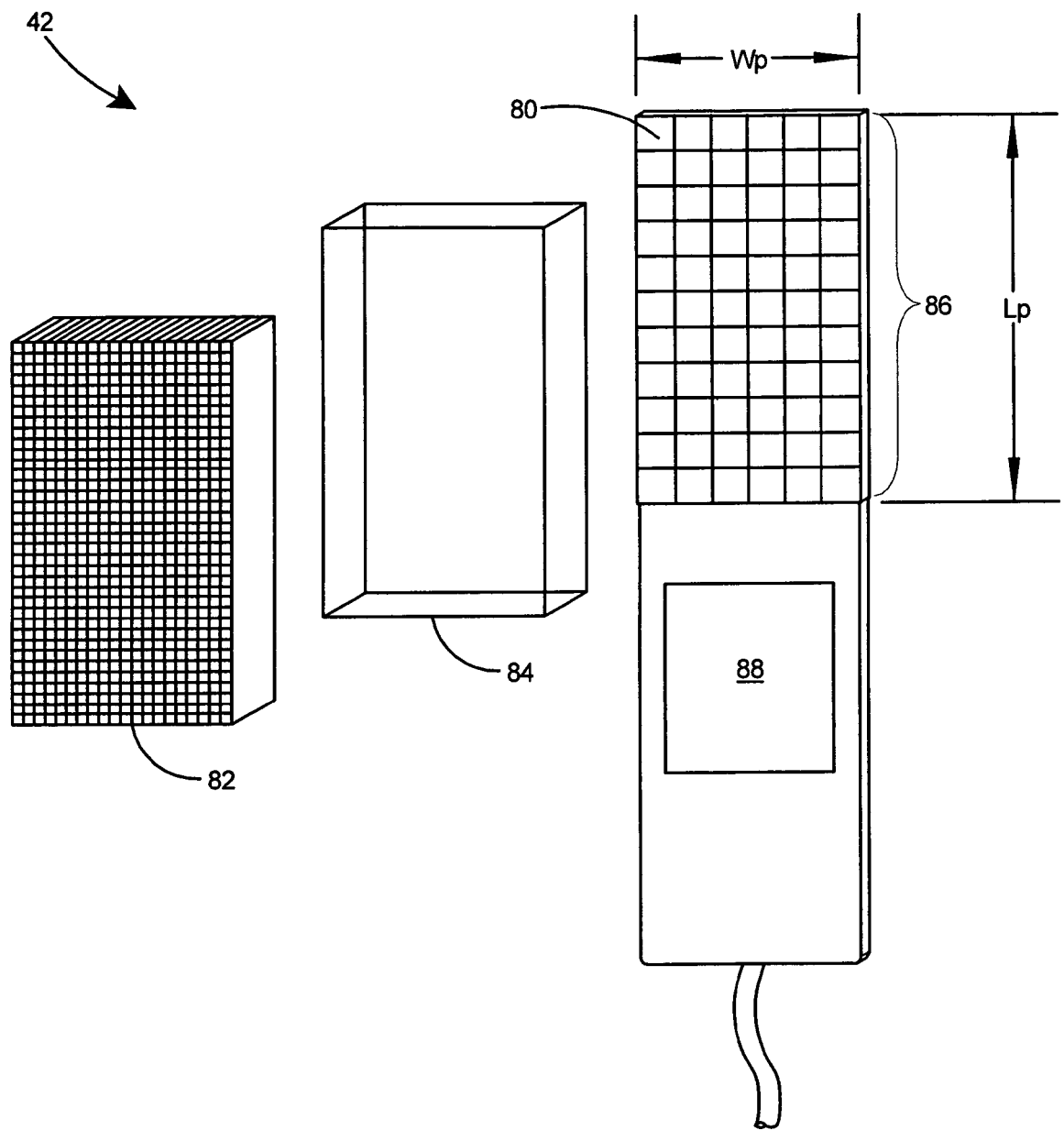
FIG. 12 is an exploded perspective view of a transrectal probe according to the present invention including an array of silicon photomultiplier or avalanche photodiodes.

With reference to FIG. 12 there is shown a schematic of such an imaging transrectal probe 42 built with SiPM sensor units 80. The probe 42 includes a scintillator array 82, a light guide 84, an SiPM array 86, and a preamplifier 88. In the SiPM array 86, an array of Silicon photomultiplier 80 or avalanche photodiodes, each assumed to occupy approximately 5 mm$^2$, covers an active field of view of 2.5 cm width (Wp) by 5 cm length (Lp). Thus the small size of the probe detector head allows the transrectal probe to be provided in a compact package. The SiPM array 86 size is 6×11 for a total of 66 pixels with a pixel frame size of 3.85×4.35 mm. The readout of the scintillation array 82, which is 1.5 mm pitch and 10 mm thick, is obtained by coupling the scintillation array 82 to the photodetector array 86 via light spreader optical window 84. With the step of 5 mm, the active size of each photodetector element 80 in the photodetector array 86 is only approximately 3 mm×3 mm. The readout with 3 mm sensor elements used on an approximate 4.3 (x) by 4.8 mm (y) pitch and with optical light guide window 84 provides excellent sampling of the scintillation signal to obtain a strong detection signal and good quality imaging capability via light sharing, while allowing for required mechanical packaging of the individual sensors used in the current generation of these devices. The probe 42 can be battery operated and also with wireless data transfer to limit the cabling necessary for its operation, however, at the expense of the size and complexity of electronics placed on board the probe.

The advantage of constructing both the external detector modules 43 and 44 and the internal transrectal probe 42 with SiPM sensor units is that such a system could be in principle used in the vicinity of or alternatively inside of an MRI magnet due to known immunity of SiPMs to strong multi-Tesla magnetic fields.

A very important and integral part of the prostate imager is the data acquisition system for accepting and digitizing signals from the readout system and then forwarding the digitized data to the computer system for data processing, data analysis and to tomographic image reconstruction. The readout system will depend on the particular choice of the technical solution selected for the imager modules, both outside and the inside probe. An example will be give below for a particular design choice for the imager.

In the preferred embodiment of the DAQ, as discussed above, the PET imager 40 as shown in FIG. 6 has four outside detector modules 45. Each detector 45 has 8 modular Hamamatsu H8500 PSPMTs coupled to a pixellated LYSO scintillator array. Each PSPMT amplifier board provides four position-encoded analog signals and one analog sum signal for a total of 40 channels per detector 45. Trigger is formed in a separate trigger hardware module. The analog sum of all PSPMTs (8) of each detector 45 is discriminated with a constant-fraction discriminator. All four discriminated signals, for each of the four detector modules, are processed by a coincidence logic circuit which provides a single coincidence trigger to four 64-channel DAQ units.

Figure 13:
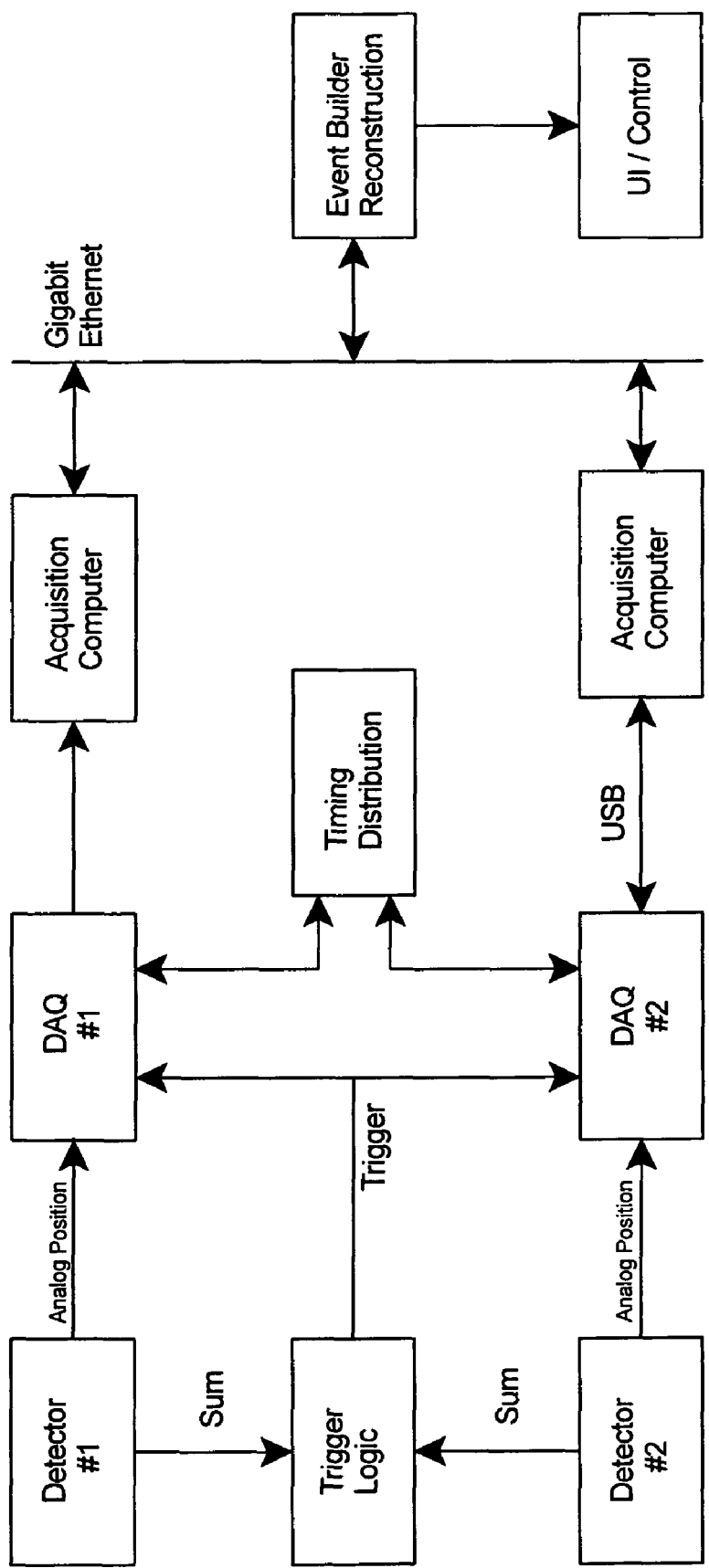
FIG. 13 is a schematic of the PET detector data acquisition system of the present invention for one coincident detector pair.

FIG. 13 is a schematic of the DAQ system of the present invention for one coincident outside detector pair. There are four combinations of coincident events between two outside modules 45 (see FIG. 6) placed above the patient 46 and two modules 45 placed under the bed 47. In addition, there are two types of coincident events between the internal transrectal probe 42 and the two outside detector modules 45 placed in front of the patient 46.

In the part of the imaging procedure without the probe 42 inserted, the event trigger will be a sum (a logical OR) of the four coincident trigger types between the four outside detectors 45. With the probe 42 inserted there will be only two types of coincident triggers involving the prostate region, however a limited imaging of the organ region in the prostate vicinity is also possible at the same time. Therefore, in principle a six-component coincident trigger option is also possible.

In case of a prostate PET imager design involving other module size combinations, different from the presently described example with four outside modules 45 and one probe 42, a different readout/DAQ system is used, matching the imager design. For example, a separate embodiment can include an imaging system with six or more modules in the outside system and a multi-component insertable probe.

A preferred embodiment for the data acquisition system is the FPGA-based USB data acquisition system designed at Jlab. This system has a modular, extensible architecture with up to 64 channels of simultaneous-sampling ADCs per unit and a sustained trigger rate of over 150 kHz for all 64 channels. In standard operation, each unit corresponds to one individual detector module. Each coincident pair of modules is time synchronized in order to match event timing of the two detectors. Both corresponding units are triggered simultaneously by the external coincidence trigger logic. Each DAQ unit sends time-stamped raw event data over high-speed USB to its own acquisition computer. Each acquisition computer performs then centroid and energy calculations on all incoming data and sends this time-stamped processed data over gigabit Ethernet to the event builder/reconstruction computer. The event builder uses the time stamps to merge the separate detector events into a single coincident event. It may also perform image reconstruction or send the data to another computer for image reconstruction. The set of reconstructed tomographic images is sent to a user interface.

A further embodiment of the prostate PET imager according to the present invention will implement time-of-flight (TOF) option when measuring timing between the coincident 511 keV gamma ray signals between all the outside detector modules and the front outside detector modules and the probe. In this PET imager, the timing is measured with such accuracy that the reconstructed volume in processed images can be smaller than the torso width. TOF PET can be used in the dedicated prostate PET imager to improve the detection of the radioactive signal emerging from the prostate, as well as other close by structures.

Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

The contents of each of the following publications are hereby incorporated in their entireties by reference:
1) N. Clinthorne, "Promise of the Compton prostate probe, recent results and beyond", presented at the Topical Symposium on Advanced Molecular Imaging Techniques in the Detection, Diagnosis, Therapy, and Follow-Up of Prostate Cancer, 6-7 Dec. 2005, Rome, Italy.
2) J. S. Huber et al., "Dual-Modality PET/Ultrasound imaging of the Prostate", Lawrence Berkeley National Laboratory. Paper LBNL-59114. (Nov. 11, 2005).
3) J. S. Huber et al., "Initial Results of a Positron Tomograph for Prostate Imaging", IEEE Transactions on Nuclear Science, Volume 53, Issue 5, Part 1, October 2006 Page(s): 2653-2659.
4) S. S. Huh et al., "Investigation of an internal PET probe for prostate imaging", accepted for publication in Nuclear Instruments and Methods in Physics Research, 2007.
5) C. Levin, "New Photon Sensor Technologies for PET in Prostate-Specific Imaging Configurations", presented at the Topical Symposium on QAdvanced Molecular Imaging Techniques in the Detection, Diagnosis, Therapy, and Follow-Up of Prostate Cancer, 6-7 Dec. 2005, Rome, Italy.
6) W. Moses, "Dedicated PET Instrumentation for prostate imaging", presented at the Topical Symposium on Advanced Molecular Imaging Techniques in the Detection, Diagnosis, Therapy, and Follow-Up of Prostate Cancer, 6-7 Dec. 2005, Rome, Italy.

7) V. Popov et al., "A Novel Readout Concept for Multianode Photomultiplier Tubes with Pad Matrix Anode Layout", Nuclear Instruments and Methods in Physics Research A 567 (2006) 319-322).
8) V. Popov et al., "Study of Photonis XP1470 Nine-Channel Photomultiplier Tube For Applications in High Resolution Single Gamma and PET Imagers", presented at the 2007 IEEE MIC conference, Honolulu, Hi., Oct. 27-Nov. 3, 2007.
9) J. Proffitt et al.; "A flexible high-rate USB2 data acquisition system for PET and SPECT imaging", 2005 IEEE Nuclear Science Symposium Conference Record, Puerto Rico, Oct. 23-29, 2005, pp. 2971-2975.
10) J. Proffitt et al., "Implementation of a High-Rate USB Data Acquisition System for PET and SPECT Imaging", 2006 IEEE Nuclear Science Symposium Conference Record, San Diego, Calif., Oct. 29-Nov. 1, 2006, pp. 3063-3067.
11) T. G. Turkington et al., "PET prostate imaging with small planar detectors", T.R.Q Nuclear Science Symposium Conference Record, 2004 IEEEQ Volume 5, Issue, 16-22 Oct. 2004 Page(s): 2806-2809.

What is claimed is:

1. A dedicated mobile PET imager for imaging the prostate and surrounding organs in a patient comprising:
   a patient bed for accepting the patient;
   an open rotating gantry mounted around said patient bed and mobile with respect to said patient bed;
   a high resolution outside PET imager placed close to the patient's torso;
   said outside PET imager including two mechanically separate detector heads secured to said rotating gantry above said patient bed and two mechanically separate detector heads secured to said rotating gantry below said patient bed;
   each of said detectors capable of limited angular rotation with respect to said patient to provide full angular projective sampling of the prostate region;
   each of said detector heads including a wide field of view having a width of between 20 and 30 centimeters thereby providing a torso-wide field of view;
   an insertable compact transrectal PET probe placed in the patient in close proximity to the prostate;
   an electronic sensor positioning system on said probe and on each of said detector heads for spatially co-registering said outside PET imager and said transrectal PET probe to each other and for controlling the absolute and relative positioning of each of said outside detector heads with respect to the patient torso; and
   a high speed data acquisition system for collecting data simultaneously from said outside PET imager and said transrectal PET probe.

2. The PET imager of claim 1 wherein said detector heads are capable of being operated
   in a static mode in which said detector heads are fixed in position with respect to the patient torso; and
   in a dynamic mode in which said detector heads are rotated with respect to the patient torso to provide full angular projective sampling of the prostate region for enhanced tomographic 3D reconstruction; and
   said detector heads can be rotated to a new viewing angle with respect to said prostate and then operated in said static mode to better view the prostate region and to optimize tomographic 3D spatial resolution.

3. The PET imager of claim 1 wherein said transrectal probe provides closer high sensitivity and very high resolution 2D view of the prostate and immediate surroundings.

4. The PET imager of claim 1 wherein said transrectal probe includes a high efficiency and a resolution of at least 1 mm FWHM.

5. The PET imager of claim 1 wherein said outside imager includes a 3D reconstruction resolution of between 1.5 to 2.0 mm over the body slice involved.

6. The PET imager of claim 1 wherein said probe in coincidence with said outside imager includes a 2D reconstruction resolution of between 1.0 to 1.5 mm over the small field of view of said probe.

7. The PET imager of claim 1 wherein said rotating gantry enables 360 degree angular sampling in a 3D imaging mode with said outside imager.

8. The PET imager of claim 1 wherein said data acquisition system is a multi-channel fast data acquisition and processing system capable of recording data with at least 200 kHz trigger rate in a list mode to enable prompt limited data analysis and fast data replay and image reconstruction during the same scan session.

9. The PET imager of claim 1 wherein said detector heads include
   a scintillator gamma sensor as a sensor/energy converter of 511 keV gamma rays; and
   a photodetector as detector of the scintillation light produced by the absorbed 511 keV gamma rays in the scintillator gamma sensor.

10. The PET imager of claim 9 wherein said scintillator gamma sensor includes pixellated or plate crystal scintillator materials selected from the group including LSO, LYSO, GSO, BGO, LaBr3, NaI(Tl), CsI(Tl), and CsI(Na).

11. The PET imager of claim 9 wherein said photodetector is selected from the group including standard photomultiplier, multi-element photomultiplier, position sensitive photomultiplier, flat panel photomultiplier, microchannel plate based photomultiplier, avalanche photodiode array, large size avalanche photodiode with resistive readout, silicon photomultiplier, simple plate light guides such as simple plates, fiberoptic straight or tapered light guides, bunches of straight or bent fibers can be used.

12. The PET imager of claim 1 wherein said transrectal probe includes
   a scintillator gamma sensor as a sensor/energy converter of 511 keV gamma rays; and
   a photodetector as detector of the scintillation light produced by the absorbed 511 keV gamma rays in the scintillator gamma sensor.

13. The PET imager of claim 12 wherein said scintillator gamma sensor includes pixellated or plate crystal scintillator materials selected from the group including LSO, LYSO, GSO, BGO, LaBr3, NaI(Tl), CsI(Tl), and CsI(Na).

14. The PET imager of claim 12 wherein said photodetector is a solid state photodetector selected from the group including avalanche photodiode and silicon photomultiplier.

15. The PET imager of claim 1 wherein said outside imager includes
   a continuous array of flat PSPMT units coupled to a scintillator sensor in the form of a pixellated array;
   said pixellated array including an array of 24×24 LYSO 2×2×15 mm pixels with a 2.1 mm pitch; and
   a coupler window between said array of PSPMT units and said pixellated array to enable better optical coupling of the light emerging from the scintillator pixels that are in front of the dead regions between individual flat PSPMT units.

16. The PET imager of claim 1 wherein said outside imager includes a SiPM photodetector having an approximate 5 cm×5 cm active FOV using approximate 12.5 mm modules; and each of said 12.5 mm modules composed of sixteen 3 mm×3 mm readout pixels arranged in a 4×4 array.

17. The PET imager of claim 1 wherein said transrectal probe includes a scintillator array including a pixel size of 1.5 mm pitch by 10 mm;

a photodetector array including an array of silicon photomultiplier or avalanche photodiodes covering an active FOV of 2.5 cm×5 cm; and a light spreader optical window coupling said scintillator array to said photodetector array.

* * * * *